(12) United States Patent
Takeuchi et al.

(10) Patent No.: US 8,840,600 B2
(45) Date of Patent: Sep. 23, 2014

(54) DISPOSABLE WEARING ARTICLE WITH ELASTIC SHEETS

(75) Inventors: Mariko Takeuchi, Kagawa (JP);
Toshifumi Otsubo, Kagawa (JP);
Tatsuya Hashimoto, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 167 days.

(21) Appl. No.: 13/509,814

(22) PCT Filed: Dec. 15, 2010

(86) PCT No.: PCT/JP2010/007273
§ 371 (c)(1),
(2), (4) Date: May 15, 2012

(87) PCT Pub. No.: WO2011/077666
PCT Pub. Date: Jun. 30, 2011

(65) Prior Publication Data
US 2012/0226255 A1    Sep. 6, 2012

(30) Foreign Application Priority Data

Dec. 22, 2009  (JP) ................................ 2009-291236

(51) Int. Cl.
*A61F 13/49*    (2006.01)
(52) U.S. Cl.
CPC ..... *A61F 13/49058* (2013.01); *A61F 13/49012* (2013.01); *A61F 13/49061* (2013.01); *A61F 13/49011* (2013.01)
USPC .................................. 604/385.3; 604/385.24
(58) Field of Classification Search
CPC .................... A61F 13/49011; A61F 13/49012; A61F 2013/49022; A61F 13/49058; A61F 13/49061
USPC .............................. 604/385.24, 385.28–385.3
See application file for complete search history.

(56) References Cited

U.S. PATENT DOCUMENTS 6,991,623 B2    1/2006  Tanaka et al.
7,066,921 B2 *  6/2006  Schmoker et al. ....... 604/385.01
(Continued)

FOREIGN PATENT DOCUMENTS

EP    2322127 A1    5/2011
JP    58128906 U    9/1983
(Continued)

OTHER PUBLICATIONS

International Search Report and Written Opinion for PCT/JP2010/007273, dated Mar. 22, 2011.

(Continued)

*Primary Examiner* — (Jackie) Tan-uyen T Ho
*Assistant Examiner* — Kathryn E Ditmer
(74) *Attorney, Agent, or Firm* — Lowe Hauptman & Ham LLP (57) ABSTRACT

A chassis of a diaper includes a first outer sheet defining a front waist region and a part of a crotch region, a second outer sheet defining a rear waist region and a part of the crotch region and a middle sheet connecting these sheets and defining a part of the crotch region. To the skin-facing side of the chassis, a liquid-absorbent structure is attached. The liquid-absorbent structure is provided with first and second elastic sheets overlapping front and rear ends of the liquid-absorbent structure, respectively. The first elastic sheet is attached under tension in a transverse direction and in contractible manner between a bottom surface of the liquid-absorbent structure and the first outer sheet and the second elastic sheet is located on a skin-facing surface of the liquid-absorbent structure and attached thereto under tension in the transverse direction and in contractible manner.

16 Claims, 4 Drawing Sheets

(56) References Cited

U.S. PATENT DOCUMENTS

| | | | |
|---|---|---|---|
| 2001/0018580 A1* | 8/2001 | Suzuki et al. | 604/385.28 |
| 2005/0137550 A1 | 6/2005 | Schmoker et al. | |
| 2005/0177126 A1* | 8/2005 | Kurata | 604/387 |
| 2006/0254708 A1* | 11/2006 | Wada et al. | 156/259 |
| 2007/0203468 A1* | 8/2007 | Inoue et al. | 604/378 |
| 2008/0287897 A1* | 11/2008 | Guzman Reyes et al. | 604/365 |
| 2009/0312732 A1* | 12/2009 | LaVon et al. | 604/378 |
| 2011/0178489 A1* | 7/2011 | Baba et al. | 604/385.3 |

FOREIGN PATENT DOCUMENTS

| | | |
|---|---|---|
| JP | 63014506 U | 1/1988 |
| JP | 11318978 A | 11/1999 |
| JP | 2001037809 A | 2/2001 |
| JP | 2002301104 A | 10/2002 |
| JP | 2008023116 A | 2/2008 |
| JP | 2008228835 A | 10/2008 |

OTHER PUBLICATIONS

Supplementary European Search Report dated Jul. 18, 2014, corresponds to European patent application No. 10838906.5.

* cited by examiner

DISPOSABLE WEARING ARTICLE WITH ELASTIC SHEETS

RELATED APPLICATIONS

The present application is a National Phase of International Application Number PCT/JP2010/007273, filed Dec. 15, 2010, and claims priority from Japanese Application Number 2009-291236, filed Dec. 22, 2009.

TECHNICAL FIELD

The present disclosure relates to disposable wearing articles and particularly to disposable wearing articles such as disposable diapers, disposable toilet-training pants, disposable incontinent pants or disposable menstruation pants using elastic sheets for waist regions of the wearing articles.

BACKGROUND ART

Conventionally, it is known to use elastic sheets for waist regions and thereby to elasticize the waist regions in a transverse direction. For example, the disposable diaper disclosed in PATENT DOCUMENT 1 (JP 2008-228835 A) has a chassis formed of an inner sheet made of a non-elastic sheet and an outer sheet made of an elastic sheet.

In the case of the diaper disclosed in PATENT DOCUMENT 1 (JP 2008-228835 A), the elastic sheet is present on the bottom surface of the liquid-absorbent structure in the front waist region as well as in the rear waist region. In consequence, the liquid-absorbent structure is compressed toward the wearer's body and in close contact with the wearer's body under contractile force of the elastic sheet in the front waist region as well as in the rear waist region. Certainly, such arrangement is effective to prevent urine leakage. However, excessively close contact of the liquid-absorbent structure with the wearer's body may cause stuffiness to be generated within the diaper and such stuffiness may cause the wearer's skin to suffer from skin irritation.

Therefore, it is desired to provide disposable wearing articles adapted to prevent urine leakage, to improve breathability of the article, to restrict generation of stuffiness within the diaper and to protect the wearer from skin irritation due to such stuffiness.

CITATION LIST

Patent Literature

[PLT 1] JP 2008-228835 A

SUMMARY OF INVENTION

A disposable wearing article in accordance with one or more embodiments of the present invention comprises a chassis which has a longitudinal direction, a transverse direction, a skin-facing side, a non-skin-facing side, a first waist region corresponding to one of front and rear waist regions, a second waist region corresponding to the other of the front and rear waist regions and a crotch region extending between the first and second waist regions, a liquid-absorbent structure extending across the crotch region into the first and second waist regions and elastic sheets which are respectively provided in the first and second waist regions to be contractible in the transverse direction.

In this article, the liquid-absorbent structure has a bottom surface facing the chassis and a skin-facing surface lying on the skin-facing side; the elastic sheets comprises a first elastic sheet lying in the first waist region and a second elastic sheet lying in the second waist region; and the first elastic sheet is bonded to the bottom surface of the liquid-absorbent structure and the second elastic sheet is bonded to the skin-facing surface of the liquid-absorbent structure.

DETAILED DESCRIPTION

Figure 1:
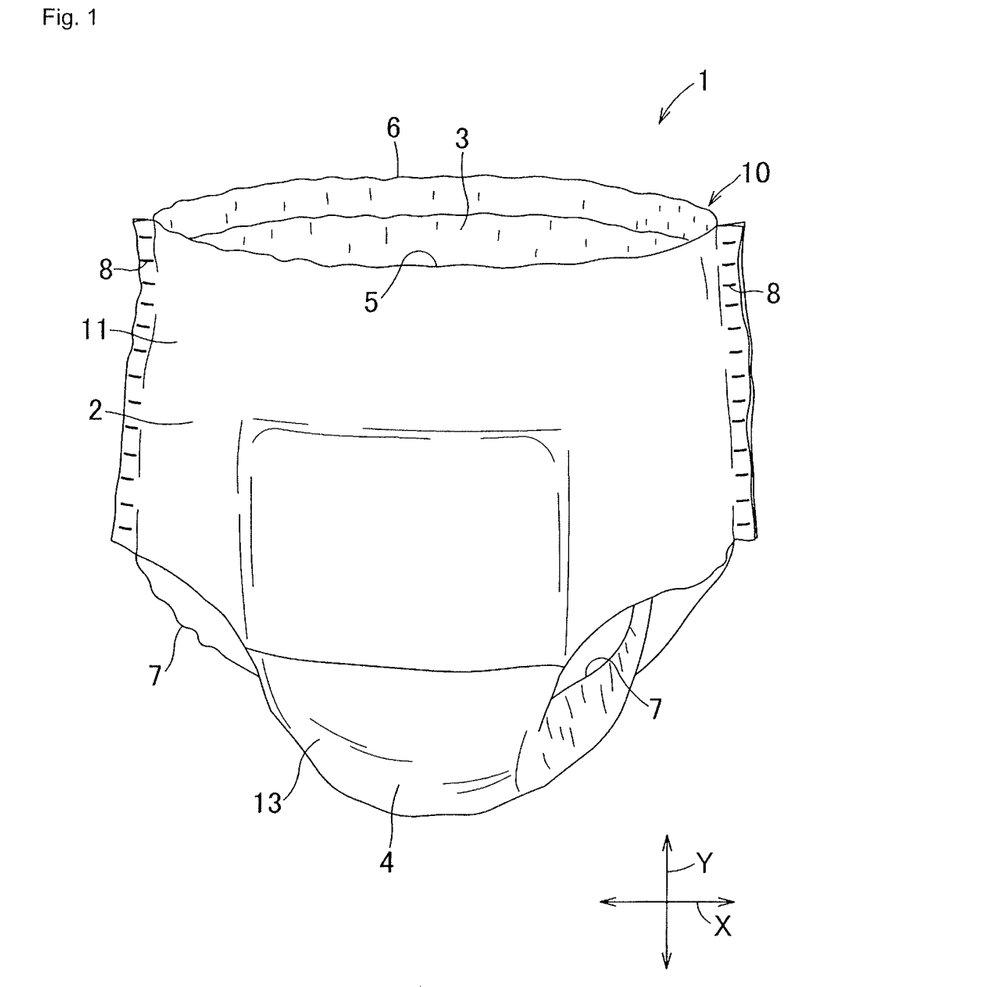
FIG. 1 is a perspective view of a diaper as one example of disposable wearing articles.
Figure 2:
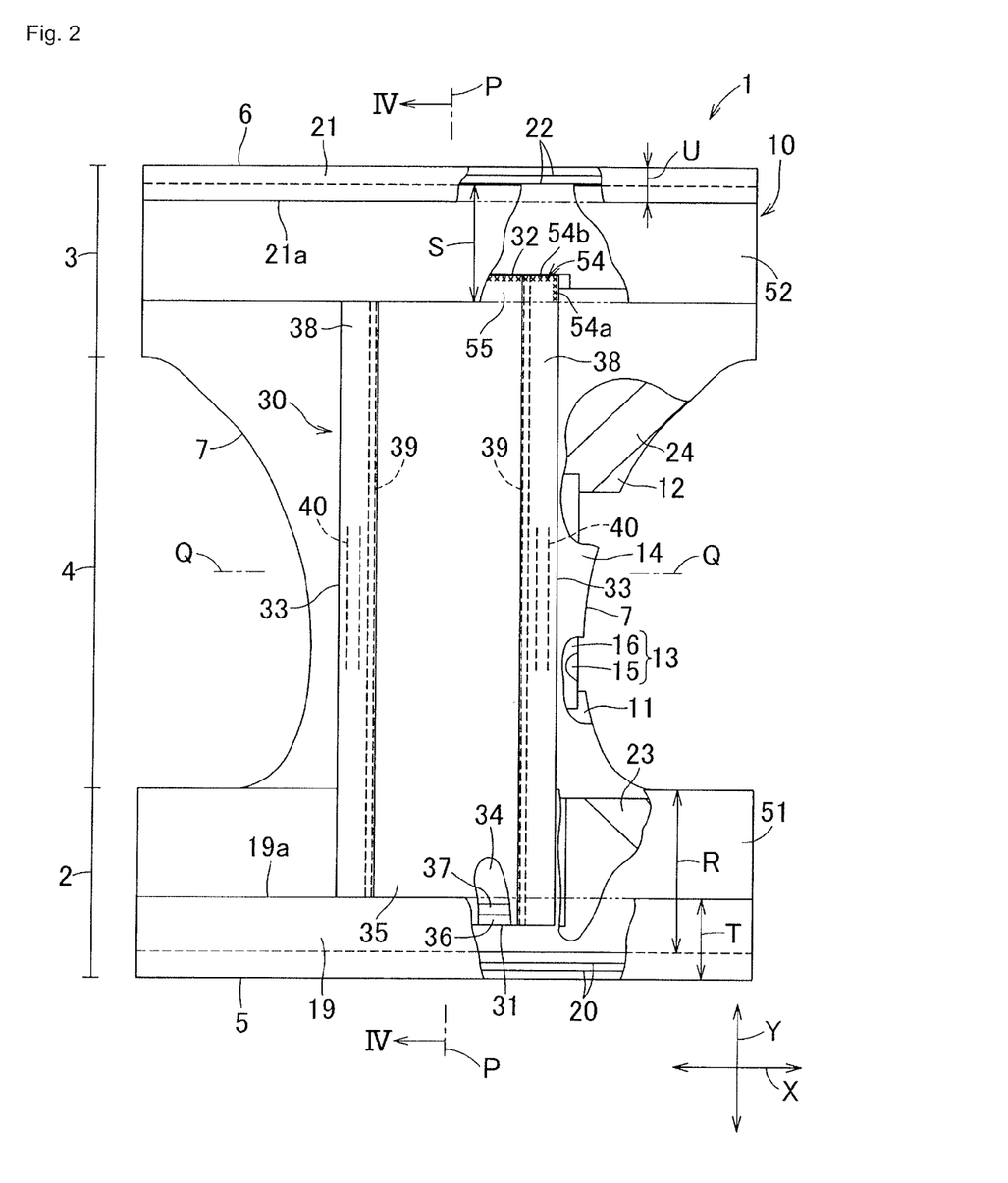
FIG. 2 is a partially cutaway plan view showing the diaper as having been flatly developed.
Figure 3:
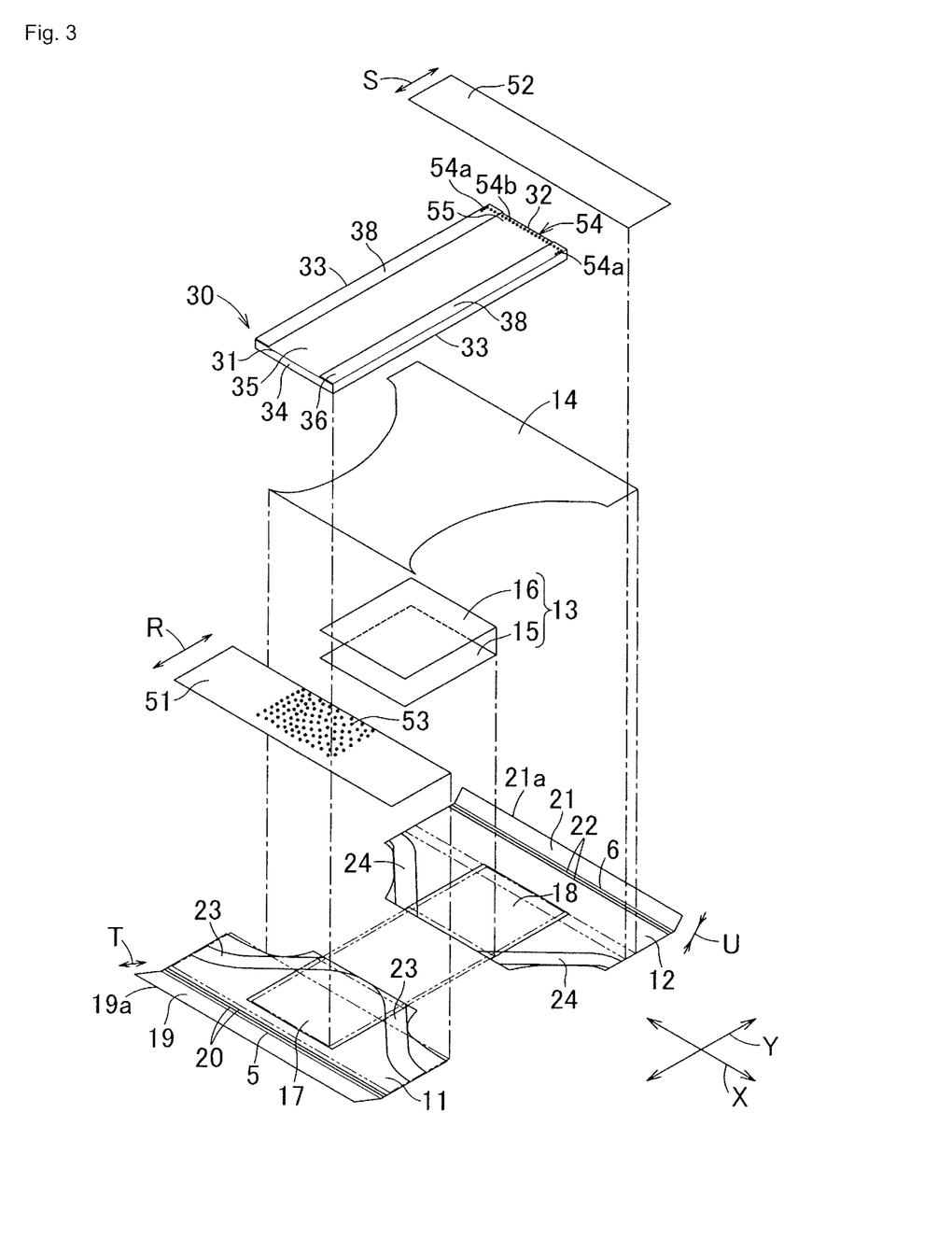
FIG. 3 is an exploded perspective view of the diaper.
Figure 4:
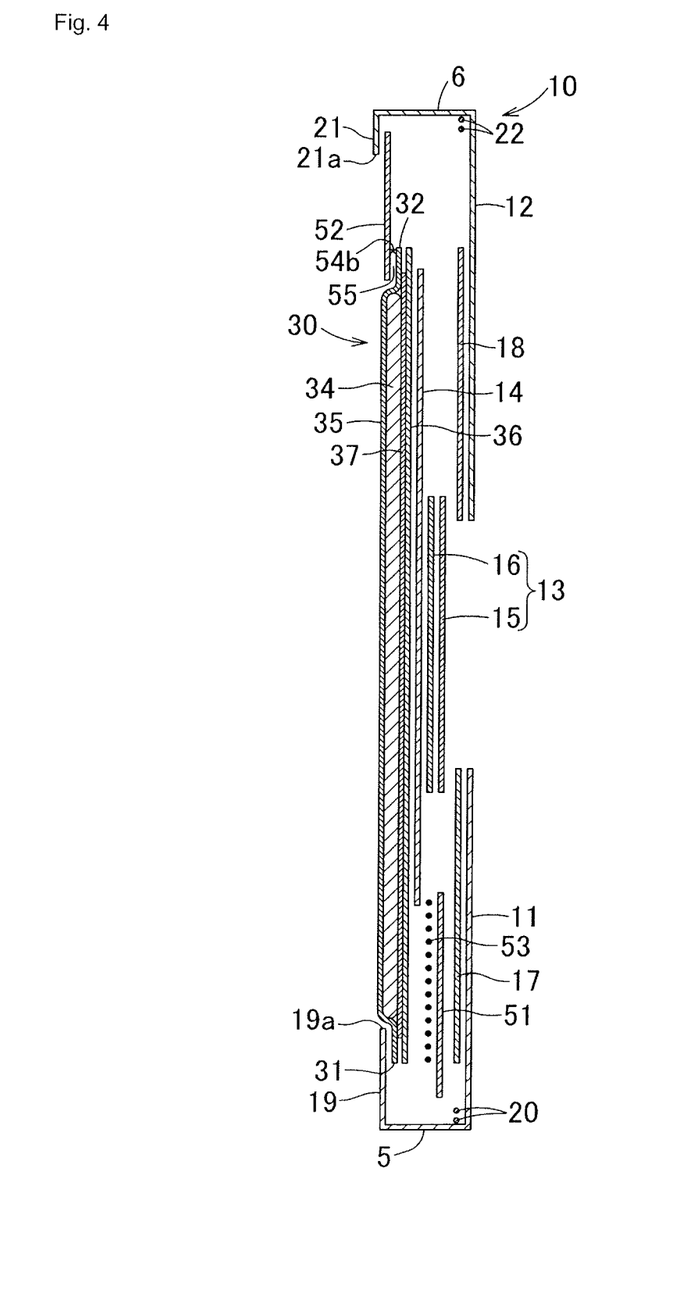
FIG. 4 is a schematic sectional view taken along the line IV-IV in FIG. 2.

As shown in FIGS. 1-4, the diaper 1 has a skin-facing side and a non-skin-facing side and comprises a chassis 10 defining an outer shape of the diaper 1, a liquid absorbent structure 30 and first and second elastic sheets 51, 52 each lying on the skin-facing side of the chassis 10.

The diaper 1 has a front waist region 2 (first waist region), a rear waist region 3 (second waist region), a crotch region 4 extending between the front and rear waist regions 2, 3, front and rear ends 5, 6 opposed to each other about the imaginary transverse center line Q-Q and extending in the transverse direction X, and side edges 7, 7 opposed to each other about the imaginary longitudinal center line P-P.

The opposite side edges 7, 7 describe concave curves in the crotch region 4 to fit around the wearer's thighs. The opposite side edges of the front waist region 2 are connected with the associated opposite side edges of the rear waist region 3 at side seam spots 8 arranged along the respective side edges intermittently in the longitudinal direction Y to form a waist-opening and a pair of leg-openings (See FIG. 1).

The chassis 10 comprises a first outer sheet 11 on the non-skin-facing side and defining the front waist region 2 and a part of the crotch region 4 and a second outer sheet 12 defining the rear waist region 3 and a part of the crotch region 4. The first and second outer sheets 11, 12 have respective skin-facing sides and non-skin-facing sides wherein graphic displaying film sheets 17, 18 printed with graphics or the like (not shown) which can be visually recognized through these first and second outer sheets 11, 12 from the outside are provided on the skin-facing sides of the first and second outer sheets.

The first and second outer sheets 11, 12 are formed of a fibrous non-woven fabric. It is possible to form these first and second outer sheets 11, 12 with multiple layers, respectively, where at least the outermost layer in each of the multiple layers comprises crimped fibers such as spun bonded filament fibers. Use of crimped fibers for the first and second outer sheets 11, 12 advantageously allows the first and second outer sheets 11, 12 to be put in close contact with the wearer's skin to provide for improved texture because the crimped fibers have elastic stretch properties.

The chassis 10 further comprises a middle sheet 13 extending between the first and second outer sheets 11, 12 to connect these two sheets 11, 12 to each other and defining a part of the crotch region 4. The middle sheet 13 comprises, in turn, a generally rectangular fibrous non-woven fabric sheet 15 facing the first and second outer sheets 11, 12 and a moisture-pervious but liquid-impervious plastic sheet 16 lying on the skin-facing side of the fibrous non-woven fabric sheet 15 and being generally the same as the fibrous non-woven fabric sheet 15 in shape as well as in size, wherein these two sheets 15, 16 are bonded to each other by hot melt adhesive (not shown). A fixing sheet 14 formed of a fibrous non-woven fabric is attached to the inner surface of the middle sheet 13 facing the wearer's body and completely covers the middle sheet 13. The fixing sheet 14 has a width dimension larger than that of the middle sheet 13 and extends to occupy the crotch region 4 and the rear waist region 3. The middle sheet 13 and the fixing sheet 14 may be formed, for example, of a spun bonded fibrous non-woven fabric made of crimped fibers similarly to the first and second outer sheets 11, 12 or may be formed, for example, of an air-through fibrous non-woven fabric having no elastic stretch properties.

In the front waist region 2, the first outer sheet 11 is folded in the longitudinal direction Y along the front end edge 5 (first end edge) to form a front folded region 19 on the skin-facing side. Within the front folded region 10, two or more elastic strands 20 as waist elastic members made of an elastomeric material are attached in a contractible manner to be associated with a front waist region. In the rear waist region 3, the second outer sheet 12 is folded in the longitudinal direction Y along the rear end edge 6 (second end edge) to form a rear folded region 21 on the skin-facing side. Within the rear folded region 21, two or more elastic strands 22 as waist elastic members made of an elastomeric material are attached in a contractible manner to be associated with a rear waist region. The elastic strands 20 for the front waist region and the elastic strands 22 for the rear waist region are attached by hot melt adhesive (not shown) under tension to extend along the front and rear end edges 5, 6, respectively, in the transverse direction X.

The first outer sheet 11 is provided with a pair of elastic tapes 23, 23 attached in a contractible manner to the inner surface of the first outer sheet 11 to extend along the side edges 7, 7 of the crotch region 4 and to be associated with respective front halves of the leg-openings. The second outer sheet 12 is provided with a pair of elastic tapes 24, 24 attached in a contractible manner to the inner surface of the second outer sheet 12 to extend along the side edges 7, 7 of the crotch region 4 and to be associated with respective rear halves of the leg-openings. The fixing sheet 14 is laminated on the first and second outer sheet 11, 12 so that parts of the respective front halves of the leg-openings and the entire rear halves of the leg-openings are covered with the fixing sheet 14. These elastic members 23, 24 associated with the front and rear halves of the respective leg-openings allow the peripheral edges of the leg-openings to be held in close contact around the wearer's thighs.

The liquid-absorbent structure 30 extending across the crotch region 4 into the front and rear waist regions 2, 3 is attached to the skin-facing side of the chassis 10. The liquid-absorbent structure 30 has a rectangular shape which is longer in the longitudinal direction Y than in the transverse direction X and comprises a bottom surface facing the chassis 10, the skin-facing surface opposed to the bottom surface, front and rear ends 31, 32 extending in the transverse direction X and opposite side edges 33, 33 extending in the longitudinal direction Y. The liquid-absorbent structure 30 extends across the crotch region 4 into the front and rear waist regions 2, 3. More specifically, the front end 31 lies over the inner surface of the first outer sheet 11, the rear end 32 lies over the inner surface of the second outer sheet 12 and a middle section extending between these front and rear ends 31, 32 lies over the inner surface of the middle sheet 13.

The liquid-absorbent structure 30 comprises a liquid-absorbent core assembly 34 formed by wrapping a mixture, for example, of fluff pulp fibers and super-absorbent polymer particles with a liquid-dispersant sheet (not shown), a liner 35 lying on the skin-facing side facing to cover a functioning surface of the liquid-absorbent core assembly 34, a cover sheet 36 adapted to cover the bottom side of the liquid-absorbent core assembly 34 and a leak-barrier sheet 37 made of a plastic material sandwiched between the cover sheet 36 and the liquid-absorbent core assembly 34.

The cover sheet 36 extends outward in the transverse direction X from opposite side edges 33 of the liquid-absorbent core assembly 34 and these portions extending from the side edges 33 are partially folded toward the imaginary longitudinal center line P-P to form a pair of sleeve-like leak-barrier cuffs 38. Within the respective leak-barrier cuffs 38, elastic strands 39, 40 made of an elastomeric material extending in the longitudinal direction Y are attached in a contractible manner to the cover sheet 36 by hot melt adhesive (not shown). More specifically, within each of the leak-barrier cuffs 38, there are provided a plurality of the elastic strands 39 and a plurality of the elastic strands 40 outboard of the elastic elements 39 as viewed in the transverse direction X. The elastic strands 39 extend across the crotch region 4 into the front and rear waist regions 2, 3. Under contraction of these elastic strands 39, leak-barrier cuffs 38 of the cover sheet 36 are spaced upward from the liner 35 to prevent body waste from leaking sideways. A plurality of the elastic strands 40 outboard of the elastic strands 39 extend in the longitudinal direction Y only in a middle section of the crotch region 4 to define elastic belts extending along inguinal regions of the wearer. The liquid-absorbent structure 30 is fixed to the inner surface of the chassis 10 via the outer surface of the cover sheet 36 by hot melt adhesive (not shown).

First and second elastic sheets 51, 52 cover one side of, and are attached to, the front and rear ends 31, 32, respectively, of the liquid-absorbent structure 30. The first elastic sheet 51 is provided in the front waist region 2 to be sandwiched between the bottom surface of the liquid-absorbent structure 30 and the first outer sheet 11 and is attached therebetween under tension in the transverse direction X in a contractible manner. The second elastic sheet 52 is provided in the rear waist region 3 to lie on the skin-facing side of the liquid-absorbent structure 30 and to be attached thereto by hot melt adhesive (not shown) under tension in the transverse direction X in a contractible manner. Respective opposite side edges of the first and second elastic sheets 51, 52 are flush with the respective opposite side edges of the first and second outer sheets 11, 12.

The first elastic sheet 51 has its outer surface bonded to the first outer sheet 11 by hot melt adhesive (not shown) and its inner surface bonded to the cover sheet 36 of the liquid-absorbent structure 30 in a first joining region 53. The first joining region 53 is formed of hot melt adhesive, for example, intermittently applied to a generally entire area over which the cover sheet 36 overlaps the first elastic sheet 51.

The second elastic sheet 52 extends in the longitudinal direction Y from the rear end edge 6 toward the crotch region 4 to overlap the rear end 32 of the liquid-absorbent structure 30 and extends outward in the transverse direction X from the opposite side edges 33 of the liquid-absorbent structure 30. Outside the liquid-absorbent structure 30 in the transverse direction X, the second elastic sheet 52 and the second outer sheet 12 are bonded to each other over entire area thereof, for example, by hot melt adhesive (not shown). In the middle section of the second elastic sheet 52 overlapping the liquid-absorbent structure 30, the second elastic sheet 52 is bonded to the structure 30 via a second joining region 54. The second joining region 54 comprises both side joining sub-regions 54*a* extending in the longitudinal direction Y along the respective leak-barrier cuffs 38 and an end joining sub-region 54*b* extending in the transverse direction X along the rear end 32. In a region other than these second joining regions 54, i.e., the region lying at a distance from the end joining sub-region 54*b* toward the crotch region 4 and surrounded by the end joining sub-region 54*b* and both side joining sub-regions 54*a*, the second elastic sheet 52 is left free from the liquid-absorbent structure 30 to define a non-joining region 55.

The front and rear folded regions 19, 21 are bonded to the first and second elastic sheets 51, 52, respectively. The front folded region 19 has its inner end 19*a* partially overlapping the liquid-absorbent structure 30. The front folded region is bonded to the first elastic sheet 51 and the liquid-absorbent structure 30 by bonding means such as hot melt adhesive (not shown). The front end 31 of the liquid-absorbent structure 30 may be covered with and bonded to the first outer sheet 11 forming the front folded region 19 to prevent loss of the components such as fluff pulp fibers from the liquid-absorbent core assembly 34. None of the joining regions, however, is present in the vicinity of the inner end 19*a* of the front folded region 19 and, in consequence, the inner end 19*a* of the front folded region 19 is not bonded to the liquid-absorbent structure 30. By leaving the inner end 19*a* adhesive-free flexibility of the first outer sheet 11 forming the front folded region 19 may be assured and skin-irritation which may otherwise be experienced by the wearer can be restricted. In addition, the adhesive-free region can function as a pocket adapted to prevent leak of body waste such as urine.

The inner end 21*a* of the rear folded region 21 slightly overlaps the second elastic sheet 52 and is bonded to the second elastic sheet 52 in such overlapping region by bonding means such as hot melt adhesive (not shown). The area over which the second outer sheet 12 forming the rear folded region 21 and the second elastic sheet 52 overlap each other may be minimized to maintain a desired level of breathability. While there is possibility that the breathability might be suppressed in the region in which these two sheets are laminated on each other, the lamination area may be minimized to restrict such suppression of the breathability. In addition, lamination of the first and second outer sheets 11, 12 on the first and second elastic sheets 51, 52, respectively might lower contraction percentages of the first and second elastic sheets 51, 52, respectively. However, the lamination area may be minimized to prevent the contraction percentage from being lowered due to lamination.

In the diaper 1 arranged as has been described above, the first and second elastic sheets 51, 52 are dimensioned to have respective sizes generally corresponding to the sizes of the front and rear waist regions 2, 3, respectively, and attached to the front and rear waist regions 2, 3 under tension in the transverse direction X and in a contractible manner. With such unique arrangement, the diaper 1 can be put on the wearer's body with good fitness generally over the entire areas of the front and rear waist regions 2, 3, respectively. Use of the first and second elastic sheets 51, 52 allows the diaper 1 not only to fit around the wearer's body over a larger range but also to prevent the diaper 1 from slipping down.

The first elastic sheet 51 lying under the bottom surface of the liquid-absorbent structure 30 functions to compress the liquid-absorbent structure 30 in close contact with the wearer's body. The front waist region 2 would otherwise be apt to be displaced as the wearer sits down and/or moves his or her leg or legs, but the first elastic sheet 51 functions to keep the front waist region 2 in close contact with the wearer's ventral side and thereby effectively prevents body waste such as urine from leaking along the ventral side of the wearer. By keeping the front waist region 2 in close contact with the wearer's ventral side, the liquid-absorbent structure 30 is prevented from bulging and, in consequence, the diaper 1 provides a neat and elegant appearance.

The second elastic sheet 52 lies on the skin-facing side of the liquid-absorbent structure 30 and, upon contraction, can directly come in close contact with the wearer's body to prevent body waste such as urine from leaking along the rear waist region 3. Upon contraction of the second elastic sheet 52, the liquid-absorbent structure 30 is spaced from the wearer's body to form a void space between the liquid-absorbent structure 30 and the wearer's body. In the rear waist region 3 of the diaper 1, body waste such as urine discharged by the wearer is apt to generate high humidity, causing uncomfortable stuffiness and often skin irritation. However, the liquid-absorbent structure 30 may be spaced from the wearer's body to improve the breathability and thereby to prevent the stuffiness or skin irritation due to the stuffiness. Furthermore, the second elastic sheet 52 is bonded to the respective leak-barrier cuffs 38 of the liquid-absorbent structure 30 to leave the non-joining region 55 surrounded by the joining regions 54*a*, 54*b* to form the pocket serving to prevent urine from leaking beyond the waist-opening. In this way, the desired breathability is assured to prevent the stuffiness and simultaneously leak of body waste such as urine can be prevented.

While the second elastic sheet 52 is bonded to the liquid-absorbent structure 30 by the second joining region 54, the side joining sub-regions 54*a* constituting the second joining region 54 are formed in the respective leak-barrier cuffs 38. These leak-barrier cuffs 38 are adapted to be spaced upward from the liner 35 on the skin-facing side so that the second elastic sheet 52 bonded to these leak-barrier cuffs 38 also may be spaced upward from the liner 35 facing the wearer's body as the respective leak-barrier cuffs 38 are spaced upward from the liner 35. As a consequence, the pocket formed by the non joining region 55 can be correspondingly enlarged.

Preferably, a dimension R of the first elastic sheet 51 in the longitudinal direction Y is set to be larger than a dimension S of the second elastic sheet 52 in the longitudinal direction Y. In other words, the first elastic sheet 51 located in the front waist region 2 may be dimensioned to be relatively large to ensure that the front waist region 2, which would otherwise be apt to be displaced, is reliably kept in close contact with the wearer's body. In contrast with this front waist region 2, in the rear waist region 3, the behavior of the second elastic sheet 5, to keep the rear waist region 3 in close contact with the wearer's body, can be well balanced with the behavior thereof to space the liquid-absorbent structure 30 from the wearer's body.

Preferably, a length dimension T of the front folded region 19 in the longitudinal direction Y is set to be larger than a length dimension U of the rear folded region 21 in the longitudinal direction Y. Specifically, the dimension T of the front folded region 19 may be set to extend beyond the front end 31 and the dimension U of the rear folded region 21 may be set to extend beyond the outer end of the second elastic sheet 52.

Preferably, both the first and second elastic sheets 51, 52 are formed of an elastic fibrous non-woven fabric made of thermal fusible elastomer fiber having a basis mass in a range of 20 to 50 $g/m^2$, more preferably in a range of 30 to 40 $g/m^2$ and a fiber density in a range of 0.01 to 0.04 $g/cm^3$, more preferably in a range of 0.025 to 0.035 $g/cm^3$. Specifically, a mixed fiber of thermoplastic polyurethane polymers with thermoplastic polymers other than thermoplastic polyurethane polymers, for example, styrene-based elastomers, polyolefin-based elastomers, vinyl chloride-based elastomers, amide-based elastomers, polyolefin-based polymers such as polyethylene, polypropylene or polystyrene may be used to form the first and second elastic sheets 51, 52.

It is also possible to form the first and second elastic sheets 51, 52 from a mixed fiber of elastomeric fiber and non-elastomeric fiber. Use of such a mixed fiber is effective to alleviate friction generated between the elastomeric fiber and the wearer's skin. In other words, the non-elastomeric fiber may be mixed with the elastomeric fiber to improve non-frictional contact with the wearer's skin and thereby to improve flexibility and texture of the first and second elastic sheets 51, 52. In addition, use of such mixed fiber allows stretch properties of the first and second elastic sheets 51, 52 to be adjusted. When the mixed fiber is used, the first and second elastic sheets 51, 52 comprising the mixed fiber is preferably subjected to a gear stretching process in which there elastic sheets are passed through a pair of gear rolls in advance. It should be noted here that the gear stretching process is well known to those skilled in the art. The first and second elastic sheets 51, 52 are hydrophobic, breathable and have leak-barrier property against body waste such as urine. It should be noted that it is possible to modify the first and second elastic sheets 51, 52 to become hydrophilic by appropriate treatment.

The first and second outer sheets 11, 12 are preferably formed by a thermally adhesive spun bonded fibrous nonwoven fabric having a basis mass in a range of 15 to 40 g/m$^2$, more preferably in a range of 25 to 35 g/m$^2$ and a fiber density in a range of 0.06 to 0.10 g/cm$^3$, more preferably in a range of 0.07 to 0.09 g/cm$^3$. It is also possible to form the first and second outer sheets 11, 12 with multiple layers.

To form bonding means used to form the first and second adhesive regions 53, 54 and the other bonding means, hot melt adhesive having a basis mass in a range of 1.0 to 5.0 g/m$^2$ may be applied in various well known patterns such as omega-pattern, spiral pattern, dotted pattern, wavy pattern and reticular pattern. Such application may be referred to as intermittent application. While the hot melt adhesive is not limited to a particular type, rubber-based adhesive, for example, SBS (styrene-butadiene-styrene)-based or SIS (styrene-isoprene-styrene)-based adhesive may be preferably used to protect the stretch properties of the first and second elastic sheets 51, 52 from affection of the hot melt adhesive as reliably as possible.

Materials for the respective component members constituting the diaper 1 are not limited to those described in this specification and the other materials of well known art conventionally used in the relevant technical field may be selectively used. Furthermore, the present invention is applicable, in addition to pant-type disposable diapers, also to so-called open-type disposable diapers each having the front and rear waist regions 2, 3 are not previously joined at the side seam spots 8 or the diaper in which the front waist region 2, the rear waist region 3 and the crotch region 4 are continuously formed.

The aspects of the present invention described above may be arranged in at least following items:

(i) A disposable wearing article (1) comprising:
a chassis (10) which has a longitudinal direction (Y), a transverse direction (X), a skin-facing side, a non-skin-facing side, a first waist region (2) corresponding to one of front and rear waist regions, a second waist region (3) corresponding to an other of the front and rear waist regions and a crotch region (4) extending between the first and second waist regions, a liquid-absorbent structure (30) extending across the crotch region into the first and second waist regions and elastic sheets (51, 52) which are respectively provided in the first and second waist regions to be contractible in the transverse direction, wherein:

said liquid-absorbent structure has a bottom surface facing the chassis and a skin-facing surface lying on the skin-facing side and opposed to the bottom surface;

said elastic sheets comprise a first elastic sheet (51) lying in the first waist region and a second elastic sheet (52) lying in the second waist region; and said first elastic sheet is bonded to the bottom surface of the liquid-absorbent structure and the second elastic sheet is bonded to the skin-facing surface of the liquid-absorbent structure.

The aspect of the present invention described in the above item (i) may provide one or more of the following advantageous effects: In the first waist region, the first elastic sheet serves to keep the liquid-absorbent structure in close contact with the wearer's body and, in the second waist region, the second elastic sheet directly comes in close contact with the wearer's skin and thereby to prevent leakage of body waste such as urine. In the second waist region, in addition to the effect as has been described just above, the liquid-absorbent structure is spaced from the wearer's body under the effect of the second elastic sheet and thereby makes it possible to prevent urine leakage, to improve breathability of the article, to restrict generation of stuffiness within the diaper and to protect the wearer from skin irritation due to such stuffiness.

Additionally, one or more of the following embodiments are provided in accordance with further aspects, which may be taken in combination with or in isolation from one another:

The liquid-absorbent structure may overlap the first elastic sheet and the second elastic sheet may overlap the liquid-absorbent structure.

That is, preferably, no portion of the first elastic sheet lies above the liquid-absorbent structure and no portion of the second elastic sheet lies below the liquid-absorbent structure.

The first elastic sheet is preferably bonded to the liquid-absorbent structure only on the bottom surface of the liquid absorbent structure and the second elastic sheet is bonded to the liquid-absorbent structure only on the skin-facing surface of said liquid-absorbent structure.

The first elastic sheet may be bonded to the liquid-absorbent structure in a first joining region (53) formed between the first elastic sheet and the liquid-absorbent structure.

The first joining region may extend over substantially the entire area over which the liquid-absorbent structure overlaps the first elastic sheet. The first joining region may be formed from adhesive that is intermittently applied. The adhesive may comprise hot melt adhesive.

The liquid-absorbent structure has first and second ends (31, 32) provided respectively in the first and second waist regions and extending in the transverse direction, the second elastic sheet may overlap and cover the second end and be bonded to the liquid-absorbent structure in a second joining region (54).

The second joining region may comprise both side joining sub-regions (54a) extending in the longitudinal direction along opposite side edges (33) of the liquid-absorbent structure and an end joining sub-region (54b) extending in the transverse direction along the second end and remaining area of the second elastic sheet which overlaps the liquid-absorbent structure is left free as a non-joining region (55). That is, the second elastic sheet is bonded to the liquid absorbent structure only in the side joining and end joining sub-regions.

The skin-facing surface of the liquid-absorbent structure may be formed along the opposite side edges with leak-barrier cuffs (38) extending and Contractible in the longitudinal direction and adapted to be spaced from the liquid-absorbent structure and the side joining sub-regions of the second joining region may be formed on the leak-barrier cuffs.

The chassis has first and second end edges (5, 6) provided respectively in the first and second waist regions and extending in the transverse direction and may have a folded region (19) folded in two layers along the first end edge and, on the skin-facing side, the folded region overlapping and covering the first end of the liquid-absorbent structure.

The folded region may be provided with waist elastic members (20) extending along the first end edge in the transverse direction and attached thereto under tension in contractible manner.

An inner end of the folded region may be free of adhesive, such that the folded region defines a pocket. That is, an inner end of the folded region may not be bonded to the liquid-absorbent structure.

A length dimension of the first elastic sheet in the longitudinal direction may be larger than that of the second elastic sheet.

The first and second elastic sheets may be formed of a fibrous non-woven fabric containing elastomeric fiber.

According to the embodiments in the above paragraphs, the advantageous effect(s) set forth at (a) is/are better ensured. Further advantageous effects of the respective embodiments may be obtained as discussed in the respective related descriptions.

The terms "first" and "second" used herein should be understood to be used merely for the purpose of identify paired components and locations thereof. The term "first waist region" used in the specification and Claims means one of the front and rear waist regions and the term "second waist region" means the other of the front and rear waist regions.

The invention claimed is:

1. A disposable wearing article, comprising:
    a chassis having a longitudinal direction, a transverse direction, a thickness direction, a skin-facing side, a non-skin-facing side, a first waist region corresponding to one of front and rear waist regions, a second waist region corresponding to the other of said front and rear waist regions and a crotch region extending between said first and second waist regions,
    a liquid impervious sheet at the crotch region on the non-skin-facing side,
    a liquid-absorbent structure extending across said crotch region into said first and second waist regions, and
    elastic sheets respectively provided in said first and second waist regions and contractible in said transverse direction,
wherein:
    said liquid-absorbent structure has a bottom surface facing said chassis and a skin-facing surface on said skin-facing side opposed to said bottom surface,
    said elastic sheets include a first elastic sheet lying in said first waist region and a second elastic sheet lying in said second waist region,
    said first elastic sheet is bonded to said bottom surface of said liquid-absorbent structure and said second elastic sheet is bonded to said skin-facing surface of said liquid-absorbent structure, and
    the liquid impervious sheet extends between the first and second elastic sheets in the longitudinal direction and does not overlap the first and second elastic sheets in the thickness direction of the chassis.

2. The disposable wearing article defined by claim 1, wherein
    said liquid-absorbent structure overlaps said first elastic sheet, and
    said second elastic sheet overlaps said liquid-absorbent structure.

3. The disposable wearing article defined by claim 1, wherein
    said first elastic sheet is bonded to said liquid-absorbent structure only on the bottom surface of said liquid-absorbent structure, and
    said second elastic sheet is bonded to said liquid-absorbent structure only on said skin-facing surface of said liquid-absorbent structure.

4. The disposable wearing article defined by claim 1, wherein said first elastic sheet is bonded to said liquid-absorbent structure in a first joining region formed between said first elastic sheet and said liquid-absorbent structure.

5. The disposable wearing article defined by claim 4, wherein the first joining region extends over substantially an entirety of an overlapping area where the liquid-absorbent structure overlaps the first elastic sheet.

6. The disposable wearing article defined by claim 1, wherein
    said liquid-absorbent structure has first and second ends provided respectively in said first and second waist regions and extending in said transverse direction,
    said second elastic sheet overlaps and covers said second end and is bonded to said liquid-absorbent structure in a second joining region.

7. The disposable wearing article defined by claim 6, wherein said second joining region comprises
    two side joining sub-regions extending in said longitudinal direction along opposite side edges of said liquid-absorbent structure, and
    an end joining sub-region extending in said transverse direction along said second end, and
    said second elastic sheet overlaps said second end and is free of direct joining to said liquid-absorbent structure in is a non-joining region surrounded by the two side joining sub-regions and the end joining sub-rejection.

8. The disposable wearing article defined by claim 7, further comprising leak-barrier cuffs extending along the opposite side edges of said skin-facing surface of said liquid-absorbent structure,
wherein
    said leak-barrier cuffs are contractible in said longitudinal direction and configured to be spaced from said liquid-absorbent structure, and
    said side joining sub-regions of said second joining region are formed on said leak-barrier cuffs.

9. The disposable wearing article defined by claim 8, wherein
    one of said leak-barrier cuffs comprises
        a first elastic member extending in the longitudinal direction and
        a second elastic member adjacent to the first elastic member in the traverse direction and extending in the longitudinal direction,
    the first elastic member extends into the front and rear waist regions, and
    the second elastic member extends in the crotch region and does not extend into the front and rear waist regions.

10. The disposable wearing article defined by claim 6 wherein
said chassis has
first and second end edges provided respectively in said first and second waist regions and extending in said transverse direction, and
a folded region folded into two layers along said first end edge, and
on said skin-facing side, said folded region overlaps and covers said first end of said liquid-absorbent structure.

11. The disposable wearing article defined by claim 10, wherein said folded region is provided with waist elastic members extending along said first end edge in said transverse direction and attached to the first end edge under tension in a contractible manner.

12. The disposable wearing article defined by claim 10, wherein said folded region has an inner end free of adhesive to define a pocket.

13. The disposable wearing article defined by claim 1, wherein a length dimension of said first elastic sheet in said longitudinal direction is larger than that of said second elastic sheet.

14. The disposable wearing article defined by claim 1, wherein said first and second elastic sheets are each formed of a fibrous non-woven fabric including elastomeric fibers.

15. The disposable wearing article defined by claim 1, wherein
the chassis further comprises front and rear outermost sheets in the front and rear waist regions, respectively, and
the front and rear outermost sheets are joined together by the liquid impervious sheet.

16. The disposable wearing article defined by claim 15, wherein
one of the front and rear outermost sheets is folded into two layers respectively on the skin-facing side and on the non-skin-facing side, and
the liquid impervious sheet is sandwiched between the layer on the non-skin-facing side and said liquid-absorbent structure.

* * * * *